United States Patent
Sasaki

(10) Patent No.: US 10,221,240 B2
(45) Date of Patent: *Mar. 5, 2019

(54) METHODS FOR TREATMENT OF GASTRIC CANCER

(71) Applicant: Morphotek, Inc., Exton, PA (US)

(72) Inventor: Yasutsuna Sasaki, Tokyo (JP)

(73) Assignee: Eisai, Inc., Woodcliff Lake, NJ (US)

( * ) Notice: Subject to any disclaimer, the term of this patent is extended or adjusted under 35 U.S.C. 154(b) by 49 days.

This patent is subject to a terminal disclaimer.

(21) Appl. No.: 15/345,618

(22) Filed: Nov. 8, 2016

(65) Prior Publication Data

US 2017/0121405 A1    May 4, 2017

Related U.S. Application Data

(63) Continuation of application No. 14/400,951, filed as application No. PCT/US2013/031208 on Mar. 14, 2013, now Pat. No. 9,512,223.

(60) Provisional application No. 61/647,384, filed on May 15, 2012.

(51) Int. Cl.
| | |
|---|---|
| *G01N 33/573* | (2006.01) |
| *A61K 39/00* | (2006.01) |
| *C07K 16/28* | (2006.01) |
| *G01N 33/574* | (2006.01) |
| *C07K 16/30* | (2006.01) |

(52) U.S. Cl.
CPC .......... *C07K 16/28* (2013.01); *C07K 16/3046* (2013.01); *G01N 33/57446* (2013.01); *G01N 33/57492* (2013.01); *A61K 2039/505* (2013.01); *A61K 2039/54* (2013.01); *A61K 2039/545* (2013.01); *C07K 2317/24* (2013.01); *C07K 2317/565* (2013.01); *G01N 2333/705* (2013.01)

(58) Field of Classification Search
None
See application file for complete search history.

(56) References Cited

U.S. PATENT DOCUMENTS

| 2009/0274697 A1 | 11/2009 | Grasso et al. |
| 2012/0164137 A1 | 6/2012 | Sass et al. |

FOREIGN PATENT DOCUMENTS

| WO | WO 2008-145136 A1 | 12/2008 |
| WO | WO 2012-061759 A2 | 5/2012 |
| WO | WO2012061759 | * 5/2012 |

OTHER PUBLICATIONS

Wu et al (Drugs of today 38:391-417, 2002, IDS Dec. 19, 2016, item 14 (Year: 2002).*
Farletuzumab, "Humanized Anti-FR-α Monoclonal Antibody Oncolytic", Drugs of the Future, 2008, 33(10), 841-843.
Low et al., "Folate-targeted therapeutic and imaging agents for cancer", Current Opinion in Chemical Biology, 2009, 13(3), 256-262.
Ebel et al., "Preclinical Evaluation of MORAb-003, a Humanized Monoclonal Antibody Antagonizing Folate Receptor-Alpha", Cancer Immunity, vol. 7, Mar. 2007, 6-13.
Elnakat et al., "Distribution, functionality and gene regulation of folate receptor isoforms: implications in targeted therapy", Advanced Drug Delivery Reviews, vol. 56, 2004, 1067-1084.
Davies et al., "Farletuzumab Humanized Anti-FR-a Monoclonal Antibody Oncolytic", Drugs of the Future, vol. 33(10), Oct. 2008, 841-843.
Ke et al., "The folate receptor as a molecular target for tumor-selective radionuclide delivery", Nuclear Medicine and Biology, 30(8), Nov. 2003, 811-817.
Konner et al., "Farletuzumab, a Humanized Monoclonal Antibody Against Folate Receptor a, in Epithelial Ovarian Cancer: A Phase I Study", Clinical Cancer Research, vol. 16(21), Nov. 2010, 5288-5295.
Lu et al., "Immunotherapy of folate receptor-expressing tumors: review of recent advances and future prospects", Journal of Controlled Release, 91, 2003, 17-29.
Online conversion base on publication in Cancer therapy posted 2007.
Weitman et al., "Distribution of the Folate Receptor GP38 in Normal and Malignant Cell Lines and Tissues", Cancer Research, vol. 52, Jun. 1992, 3396-3401.
Weitman et al., "Cellular Localization of the Folate Receptor: Potential Role in Drug Toxicity and Folate Homeostasis", Cancer Research, vol. 52, Dec. 1992, 6708-6711.
Wu et al., "The Immunogenetics and Pathogenesis of Gastric Gancer", Drugs of Today, 38(6), Jun. 2002, 391-417.
Macor et al., "Complement activated by chimeric anti-folate receptor antibodies is an efficient effector system to control ovarian carcinoma", Cancer Research, AACR—American Association for Cancer Research, 2006, 66(7), 3876-3883.
Zanten-Przybysz et al., "Cellular and humoral responses after multiple injections of unconjugated chimeric monoclonal antibody MOv18 in ovarian cancer patents: A pilot study", Journal of Cancer Research and Clinical Oncology, Springer International, Berlin, DE, 2002, 128(9), 484-492.

* cited by examiner

*Primary Examiner* — Lei Yao
(74) *Attorney, Agent, or Firm* — Baker & Hostetler LLP

(57) ABSTRACT

The application provides methods of detection, diagnosis, prognosis, prophylaxis and treatment of folate receptor-alpha-expressing gastric cancer using antibodies that specifically bind to folate receptor alpha.

10 Claims, 1 Drawing Sheet
Specification includes a Sequence Listing.

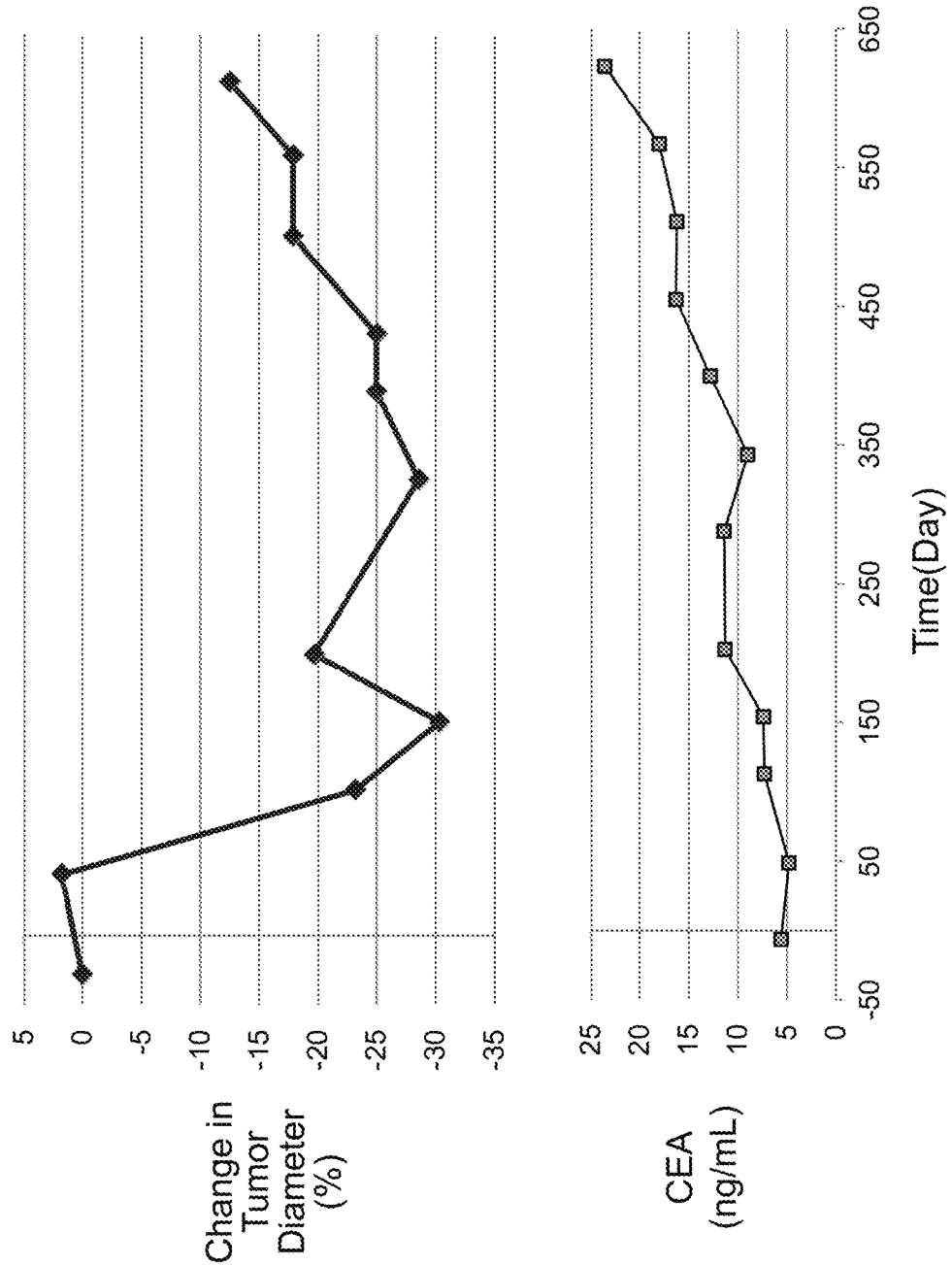

METHODS FOR TREATMENT OF GASTRIC CANCER

CROSS-REFERENCE TO RELATED APPLICATIONS

This application is a continuation of U.S. application Ser. No. 14/400,951, filed Nov. 13, 2014, now U.S. Pat. No. 9,512,223, which is the National Stage of International Application No. PCT/US2013/031208, filed Mar. 14, 2013, which claims the benefit of U.S. Appl. No. 61/647,384, filed May 15, 2012, the entireties of which applications are incorporated herein by reference for any and all purposes.

SEQUENCE LISTING

The instant application contains a Sequence Listing which has been submitted electronically in ASCII format and is hereby incorporated by reference in its entirety. Said ASCII copy, created on Nov. 2, 2016, is named 104018.000962_SL.txt and is 11,802 bytes in size.

TECHNICAL FIELD

The subject matter described herein relates to methods of detection, diagnosis, prognosis, prophylaxis and treatment of folate receptor-alpha-expressing gastric cancer using antigen-binding proteins (e.g., antibodies and antigen-binding fragments thereof) that specifically bind to folate receptor alpha.

BACKGROUND

Folate (folic acid or vitamin B9) is essential for the biosynthesis of nucleotide bases and for many other methylation reactions. Folic acid is required in increased amounts by rapidly dividing cells, such as cancer cells. Folate receptors can mediate unidirectional transportation of folates into cells. Among the four isoforms of folate receptors identified (α, β, γ, and δ), α and β isoforms of folate receptor are glycosylphosphatidylinositol (GPI)-anchored proteins with two N-glycosylation sites, and both have high affinity ($K_D$ of approximately 1 nM) for folate. Elnakat et al., Adv Drug Deliv Rev 2004, 56:1067-1084.

Folate receptor alpha (also referred to as FRα, FR-alpha, FRA, FOLR-1 or FOLR1) is expressed in a variety of epithelial tissues, including those of the choroid plexus, lung, thyroid, kidney, uterus, breast, fallopian tube, epididymis, and salivary glands. Weitman, S D et al. Cancer Res 52: 3396-3401 (1992); Weitman S D et al, Cancer Res 52: 6708-6711.

Gastric or stomach cancer is a cancer that forms in tissues lining the stomach. According to the National Cancer Institute, an estimated 21,320 new cases (more than 13,000 men and 8,000 women) of stomach cancer will be diagnosed in the United States in 2012. Most diagnosed individuals will be over 70 years old. In addition, an estimated 10,540 deaths from stomach cancer will occur in the United States in 2012.

According to the World Health Organization, about 988,000 new cases of stomach cancer were estimated to have occurred in 2008, making it the fourth most common malignancy in the world. More than 70% of cases (713,000 cases) occurred in developing countries (467,000 in men, 246,000 in women). Incidence rates for stomach cancer were highest in Eastern Asia (China, Japan and Korea). Stomach cancer was the second leading cause of cancer death in both sexes worldwide (about 736,000 deaths). The highest mortality rates are estimated in Eastern Asia (28.1 per 100,000 in men, 13.0 per 100,000 in women).

Early detection and treatment of gastric cancer improves survival rates and quality of life. To improve the likelihood of early detection and treatment, a pressing need exists for non-invasive methods for diagnosing gastric cancer, for determining the level of risk of developing gastric cancer, for predicting the progression of gastric cancer, and for treating gastric cancer. The present invention satisfies these needs for folate receptor-alpha-expressing gastric cancer.

SUMMARY

Provided herein are methods for treating folate receptor-alpha-expressing gastric cancer in a subject in need thereof. The methods involve administration of a therapeutically effective amount of an anti-folate receptor antibody or an antigen-binding fragment thereof. In some embodiments, the antibody comprises a heavy chain CDR1 (CDRH1) comprising the amino acid sequences of SEQ ID NO: 1; CDR2 (CDRH2) comprising the amino acid sequences of SEQ ID NO: 2; and CDR3 (CDRH3) the amino acid sequences of comprising SEQ ID NO: 3, and light chain CDR1 (CDRL1) comprising the amino acid sequences of SEQ ID NO: 4; light chain CDR2 (CDRL2) comprising the amino acid sequences of SEQ ID NO: 5; and CDR3 (CDRL3) comprising the amino acid sequence of SEQ ID NO:6. In some preferred embodiments, the antibody is farletuzumab. In preferred embodiments, the antibody or antigen-binding fragment is delivered via intravenous administration. The antibody or antigen-binding fragment may be administered weekly. In some embodiments, the antibody or fragment is administered at a dosage of about 50 to 400 mg/m$^2$.

Also provided herein are methods of detecting folate receptor alpha-expressing gastric cancer in a biological sample. In some embodiments, the methods involve exposure of the sample to i) an antibody that specifically binds folate receptor alpha comprising a heavy chain comprising a CDR1 comprising the amino acid sequence of SEQ ID NO: 13, a CDR2 comprising the amino acid sequence of SEQ ID NO: 14, and a CDR3 comprising the amino acid sequence of SEQ ID NO: 15 and a light chain comprising a CDR1 comprising the amino acid sequence of SEQ ID NO: 9, a CDR2 comprising the amino acid sequence of SEQ ID NO: 10, and a CDR3 comprising the amino acid sequence of SEQ ID NO: 11, or an antigen-binding fragment thereof, or ii) an antibody, or antigen-binding fragment thereof, capable of binding the epitope of folate receptor alpha that is bound by an antibody that specifically binds folate receptor alpha comprising a heavy chain comprising a CDR1 comprising the amino acid sequence of SEQ ID NO: 13, a CDR2 comprising the amino acid sequence of SEQ ID NO: 14, and a CDR3 comprising the amino acid sequence of SEQ ID NO: 15 and a light chain comprising a CDR1 comprising the amino acid sequence of SEQ ID NO: 9, a CDR2 comprising the amino acid sequence of SEQ ID NO: 10, and a CDR3 comprising the amino acid sequence of SEQ ID NO: 11; followed by detection of folate receptor alpha. In some embodiments, the antibody, or antigen-binding fragment, is affixed to a solid support.

Further provided are methods for treating folate receptor-alpha-expressing gastric cancer in a subject in need thereof by detecting folate receptor alpha-expressing gastric cancer in a biological sample by exposing the sample to a first antibody antibody that specifically binds folate receptor alpha or an antigen-binding fragment thereof, detecting folate receptor alpha, and administering to the subject a therapeutically effective amount of a second antibody that specifically binds folate receptor alpha or an antigen-binding fragment thereof. In some embodiments, the first antibody that specifically binds folate receptor alpha comprises a heavy chain comprising a CDR1 comprising the amino acid sequence of SEQ ID NO: 13, a CDR2 comprising the amino acid sequence of SEQ ID NO: 14, and a CDR3 comprising the amino acid sequence of SEQ ID NO: 15 and a light chain comprising a CDR1 comprising the amino acid sequence of SEQ ID NO: 9, a CDR2 comprising the amino acid sequence of SEQ ID NO: 10, and a CDR3 comprising the amino acid sequence of SEQ ID NO: 11. In some embodiments, the first antibody that specifically binds folate receptor alpha is an antibody capable of binding the epitope of folate receptor alpha that is bound by an antibody that specifically binds folate receptor alpha comprising a heavy chain comprising a CDR1 comprising the amino acid sequence of SEQ ID NO: 13, a CDR2 comprising the amino acid sequence of SEQ ID NO: 14, and a CDR3 comprising the amino acid sequence of SEQ ID NO: 15 and a light chain comprising a CDR1 comprising the amino acid sequence of SEQ ID NO: 9, a CDR2 comprising the amino acid sequence of SEQ ID NO: 10, and a CDR3 comprising the amino acid sequence of SEQ ID NO: 11. The first antibody or antigen-binding fragment is optionally affixed to a solid support. In some embodiments, the second antibody that specifically binds folate receptor alpha comprises a heavy chain CDR1 (CDRH1) comprising the amino acid sequence of SEQ ID NO: 1; CDR2 (CDRH2) comprising the amino acid sequence of SEQ ID NO: 2; and CDR3 (CDRH3) comprising the amino acid sequence of SEQ ID NO: 3, and light chain CDR1 (CDRL1) comprising the amino acid sequence of SEQ ID NO: 4; light chain CDR2 (CDRL2) comprising the amino acid sequence of SEQ ID NO: 5; and CDR3 (CDRL3) comprising the amino acid sequence of SEQ ID NO:6. In preferred embodiments, the second antibody is farletuzumab. The step of administering may involve intravenous injection of said second antibody or antigen-binding fragment. The step of administering may comprise weekly administration of the second antibody or antigen-binding fragment. In some embodiments, the second antibody or antigen-binding fragment is administered at a dosage of about 50 mg/m$^2$ to about 400 mg/m$^2$, preferably a dosage of about 400 mg/m$^2$.

BRIEF DESCRIPTION OF THE DRAWINGS

FIG. 1 shows the change in the sum of the longest diameter of tumor and level of tumor marker carcinoembryonic antigen (CEA) in gastric cancer patient #16.

DETAILED DESCRIPTION OF ILLUSTRATIVE EMBODIMENTS

Various terms relating to aspects of the description are used throughout the specification and claims. Such terms are to be given their ordinary meaning in the art unless otherwise indicated. Other specifically defined terms are to be construed in a manner consistent with the definitions provided herein.

As used in this specification and the appended claims, the singular forms "a," "an," and "the" include plural referents unless the content clearly dictates otherwise. Thus, for example, reference to "a cell" includes a combination of two or more cells, and the like.

The term "antibody" refers to (a) immunoglobulin polypeptides, i.e., polypeptides of the immunoglobulin family that contain an antigen binding site that specifically binds to a specific antigen (e.g., folate receptor alpha), including all immunoglobulin isotypes (IgG, IgA, IgE, IgM, IgD, and IgY), classes (e.g. IgG1, IgG2, IgG3, IgG4, IgA1, IgA2), subclasses, and various monomeric and polymeric forms of each isotype, unless otherwise specified, and (b) conservatively substituted variants of such immunoglobulin polypeptides that immunospecifically bind to the antigen (e.g., folate receptor alpha). Antibodies are generally described in, for example, Harlow & Lane, Antibodies: A Laboratory Manual (Cold Spring Harbor Laboratory Press, 1988). Unless otherwise apparent from the context, reference to an antibody also includes antibody derivatives as described in more detail below.

"Antibody fragments" comprise a portion of a full length antibody, generally the antigen-binding or variable region thereof, such as Fab, Fab', F(ab')$_2$, and Fv fragments; diabodies; linear antibodies; single-chain antibody molecules; and multispecific antibodies formed from antibody fragments. Various techniques have been developed for the production of antibody fragments, including proteolytic digestion of antibodies and recombinant production in host cells; however, other techniques for the production of antibody fragments will be apparent to the skilled practitioner. In some embodiments, the antibody fragment of choice is a single chain Fv fragment (scFv). "Single-chain Fv" or "scFv" antibody fragments comprise the $V_H$ and $V_L$ domains of antibody, wherein these domains are present in a single polypeptide chain. Generally, the Fv polypeptide further comprises a polypeptide linker between the $V_H$ and $V_L$ domains which enables the scFv to form the desired structure for antigen binding. For a review of scFv and other antibody fragments, see James D. Marks, Antibody Engineering, Chapter 2, Oxford University Press (1995) (Carl K. Borrebaeck, Ed.).

An "antibody derivative" means an antibody, as defined above, that is modified by covalent attachment of a heterologous molecule such as, e.g., by attachment of a heterologous polypeptide, or by glycosylation, deglycosylation, acetylation or phosphorylation not normally associated with the antibody, and the like.

The term "monoclonal antibody" refers to an antibody that is derived from a single cell clone, including any eukaryotic or prokaryotic cell clone, or a phage clone, and not the method by which it is produced. Thus, the term "monoclonal antibody" is not limited to antibodies produced through hybridoma technology.

An "antigen" is an entity to which an antibody specifically binds. Folate receptor alpha is the antigen to which an anti-folate receptor-alpha antibody specifically binds.

The terms "cancer" and "tumor" are well known in the art and refer to the presence, e.g., in a subject, of cells possessing characteristics typical of cancer-causing cells, such as uncontrolled proliferation, immortality, metastatic potential, rapid growth and proliferation rate, and certain characteristic morphological features. Cancer cells are often in the form of a tumor, but such cells may exist alone within a subject, or may be non-tumorigenic cancer cells, such as leukemia cells. As used herein, the term "cancer" includes pre-malignant as well as malignant cancers.

As used herein, a "folate receptor-alpha-expressing gastric cancer" includes any type of gastric cancer characterized in that the cancer cells express or present of their surface folate receptor alpha. Folate receptor-alpha-expressing gastric cancers include, but are not limited to, gastric adenocarcinomas (e.g., intestinal type; diffuse type; papillary; tubular; poorly differentiated; signet-ring cell; and mucinous adenocarcinoma), soft tissue sarcomas (e.g., leiomyosarcomas and gastrointestinal stromal tumors), lymphomas (e.g., mucosa associated lymphoid tissue (MALT) lymphomas), carcinoid tumors, and small cell neuroendocrine carcinoma.

As used herein, a subject who is "afflicted with folate receptor-alpha-expressing gastric cancer" is one who is clinically diagnosed with such a cancer by a qualified clinician (for example, by the methods described herein), or one who exhibits one or more signs or symptoms of such a cancer and is subsequently clinically diagnosed with such a cancer by a qualified clinician (for example, by the methods described herein). A non-human subject that serves as an animal model of folate receptor-alpha-expressing gastric cancer may also fall within the scope of a subject "afflicted with folate receptor-alpha-expressing gastric cancer."

The term "inhibit" or "inhibition of" means to reduce by a measurable amount, or to prevent entirely.

The term "deplete," in the context of the effect of a folate receptor alpha antibody on folate receptor alpha-expressing cells, refers to a reduction in the number of, or elimination of, the folate receptor alpha-expressing cells.

The term "functional," in the context of an anti-folate receptor alpha antibody to be used in accordance with the methods described herein, indicates that the antibody is (1) capable of binding to folate receptor alpha and/or (2) depletes or inhibits the proliferation of folate receptor alpha-expressing cells.

The term "prophylaxis" refers to administration of an anti-folate receptor alpha antibody or antigen-binding fragment thereof to a subject before the onset of a clinical or diagnostic symptom of a folate receptor alpha-expressing gastric cancer (e.g., administration to an individual with a predisposition or at a high risk of acquiring gastric cancer) to (a) block the occurrence or onset of the folate receptor alpha-expressing gastric cancer, or one or more of clinical or diagnostic symptoms thereof, (b) inhibit the severity of onset of the folate receptor alpha-expressing gastric cancer, or (c) to lessen the likelihood of the onset of the folate receptor alpha-expressing gastric cancer.

The terms "treatment" or "treat" refer to slowing, stopping, or reversing the progression of a folate receptor alpha-expressing gastric cancer in a patient, as evidenced by a decrease or elimination of a clinical or diagnostic symptom of the disease, by administration of an anti-folate receptor alpha antibody or antigen-binding fragment thereof to the subject after the onset of a clinical or diagnostic symptom of the folate receptor alpha-expressing gastric cancer at any clinical stage. Treatment can include, for example, a decrease in the severity of a symptom, the number of symptoms, or frequency of relapse.

The term "pharmaceutically acceptable" refers to those properties and/or substances which are acceptable to the patient from a pharmacological/toxicological point of view and to the manufacturing pharmaceutical chemist from a physical/chemical point of view regarding composition, formulation, stability, patient acceptance and bioavailability and includes properties and/or substances approved by a regulatory agency of the Federal or a state government or listed in the U.S. Pharmacopeia or other generally recognized pharmacopeia for use in animals, and more particularly in humans. The term "pharmaceutically compatible ingredient" refers to a pharmaceutically acceptable diluent, adjuvant, excipient, or vehicle with which an anti-folate receptor alpha antibody is administered. "Pharmaceutically acceptable carrier" refers to a medium that does not interfere with the effectiveness of the biological activity of the active ingredient(s) and is not toxic to the host to which it is administered.

The terms "effective amount" and "therapeutically effective amount" are used interchangeably herein and, in the context of the administration of a pharmaceutical agent, refer to the amount of the agent that is sufficient to inhibit the occurrence or ameliorate one or more clinical or diagnostic symptoms of a folate receptor alpha-expressing gastric cancer in a patient. A therapeutically effective amount of an agent may vary according to factors such as the disease state, age, sex, and weight of the individual, and the ability of the antibody or antigen-binding fragment thereof to elicit a desired response in the individual. Such results may include, but are not limited to, the treatment of a folate-receptor alpha-expressing gastric cancer, as determined by any means suitable in the art. An effective amount of an agent is administered according to the methods described herein in an "effective regimen." The term "effective regimen" refers to a combination of amount of the agent and dosage frequency adequate to accomplish treatment of a folate receptor alpha-expressing gastric cancer.

The terms "patient" and "subject" are used interchangeably to refer to humans and other non-human animals, including veterinary subjects, that receive diagnostic, prophylactic or therapeutic treatment. The term "non-human animal" includes all vertebrates, e.g., mammals and non-mammals, such as non-human primates, mice, rabbits, sheep, dog, cat, horse, cow, chickens, amphibians, and reptiles. In a preferred embodiment, the subject is a human. In some embodiments, the subject is of Japanese descent.

Therapeutic agents are typically substantially pure from undesired contaminants. This means that an agent is typically at least about 50% w/w (weight/weight) purity, as well as being substantially free from interfering proteins and contaminants. Sometimes the agents are at least about 80% w/w and, more preferably at least 90 or about 95% w/w purity. However, using conventional protein purification techniques, homogeneous peptides of at least 99% purity w/w can be obtained.

I. General

The invention provides methods of detection, diagnosis, prognosis, prophylaxis and treatment and monitoring treatment of folate receptor alpha-expressing gastric cancer using antibodies to folate receptor alpha, or antigen-binding fragments thereof. The methods are premised in part on the results presented in the Examples showing that folate receptor alpha is expressed in certain gastric cancers and that long-term disease stabilization of folate receptor alpha-expressing gastric cancer can be achieved by administration of an anti-folate receptor alpha antibody.

II. Antibodies to Folate Receptor Alpha

The description that follows first considers properties of antibodies to folate receptor alpha applicable to detection of folate receptor alpha in gastric cancer and treatment thereof, and then focuses on preferred properties of antibodies for that application.

A. Antibodies to Folate Receptor Alpha in General

Anti-folate receptor alpha antibodies include monoclonal, chimeric (e.g., having a human constant region and mouse variable region), humanized, veneered, or human antibodies; single chain antibodies, or the like. The immunoglobulin molecules can be of any type or class (e.g., IgG, IgE, IgM, IgD, IgA and IgY) or subclass (e.g., IgG1, IgG2, IgG3, IgG4, IgA1 and IgA2).

Anti-folate receptor alpha antibodies can be an antigen-binding antibody fragment such as, a Fab, a F(ab'), a F(ab')$_2$, a Fd chain, a single-chain Fv (scFv), a single-chain antibody, a disulfide-linked Fv (sdFv), a fragment comprising either a $V_L$ or $V_H$ domain, including nanobodies or fragments from camels, llamas or the like, or fragments produced by a Fab expression library, or a folate receptor alpha-binding fragments of any of the above antibodies described supra. Antigen-binding antibody fragments, including single-chain antibodies, can comprise the variable region(s) alone or in combination with the entirety or a portion of the following: hinge region, CH1, CH2, CH3 and CL domains. Also, antigen-binding fragments can comprise any combination of variable region(s) with a hinge region, CH1, CH2, CH3 and CL domains. Typically, the antibodies are human, rodent (e.g., mouse and rat), donkey, sheep, rabbit, goat, guinea pig, camelid, horse, or chicken.

The antibodies can be mono-specific, bi-specific, tri-specific, or of greater multi-specificity. Multi-specific antibodies may be specific for different epitopes of folate receptor alpha or may be specific for both folate receptor alpha as well as for a heterologous protein. (See, e.g., Intl. Publ. Nos. WO 93/17715; WO 92/08802; WO 91/00360; WO 92/05793; Tutt et al., 1991, J. Immunol. 147:60-69; U.S. Pat. Nos. 4,474,893; 4,714,681; 4,925,648; 5,573,920; and U.S. Pat. No. 5,601,819; Kostelny et al., 1992, J. Immunol. 148:1547-1553.)

Anti-folate receptor alpha antibodies can also be described in terms of their binding affinity to folate receptor alpha, of $10^{-7}$M, $5\times10^{-8}$ M, $10^{-8}$ M, $5\times10^{-9}$ M, $10^{-9}$M, $5\times10^{-10}$ M, $10^{-10}$ M, $5\times10^{-11}$ M, $10^{-12}$ M, $5\times10^{-12}$ M, $10^{-12}$ M, $5\times10^{-13}$ M, $10^{-13}$ M, $5\times10^{-14}$ M, $10^{-14}$M, $5\times10^{-15}$M, or $10^{-15}$ M.

An anti-folate receptor alpha antibody can be a chimeric antibody. A chimeric antibody is a molecule in which different portions of the antibody are derived from different animal species, such as antibodies having a variable region derived from a murine monoclonal antibody and a human immunoglobulin constant region. Methods for producing chimeric antibodies are known in the art. (See, e.g., Morrison, Science, 1985, 229:1202; Oi et al., 1986, BioTechniques 4:214; Gillies et al., 1989, J. Immunol. Methods 125:191-202; U.S. Pat. Nos. 5,807,715; 4,816,567; and 4,816,397.)

An anti-folate receptor alpha antibody can also be a humanized antibody including a veneered antibody. Humanized antibodies are antibody molecules that bind the desired antigen and have one or more complementarity determining regions (CDRs) from a non-human species, and framework and constant regions from a human immunoglobulin molecule. Often, framework residues in the human framework regions will be substituted with the corresponding residue from the CDR donor antibody to alter, or preferably improve, antigen binding. These framework substitutions are identified by methods well known in the art, e.g., by modeling of the interactions of the CDR and framework residues to identify framework residues important for antigen binding and sequence comparison to identify unusual framework residues at particular positions. (See, e.g., Queen et al., U.S. Pat. No. 5,585,089; Riechmann et al., 1988, Nature 332:323.) Antibodies can be humanized using a variety of techniques known in the art such as CDR-grafting (EP 0 239 400; WO 91/09967; U.S. Pat. Nos. 5,225,539; 5,530,101; and 5,585,089), veneering or resurfacing (EP 0 592 106; EP 0 519 596; Padlan, Molecular Immunology, 1991, 28(4/5):489-498; Studnicka et al., 1994, Protein Engineering 7(6):805-814; Roguska et al., 1994, PNAS 91:969-973), and chain shuffling (U.S. Pat. No. 5,565,332) (all of these references are incorporated by reference herein).

An anti-folate receptor alpha antibody can also be a human antibody. Human antibodies can be made by a variety of methods known in the art such as phage display methods using antibody libraries derived from human immunoglobulin sequences. See also, e.g., U.S. Pat. Nos. 4,444,887 and 4,716,111; WO 98/46645, WO 98/50433, WO 98/24893, WO 98/16654, WO 96/34096, WO 96/33735, and WO 91/10741. In addition, a human antibody recognizing a selected epitope can be generated using a technique referred to as "guided selection," in which a selected non-human monoclonal antibody, e.g., a mouse antibody, is used to guide the selection of a completely human antibody recognizing the same epitope (see, e.g., Jespers et al., 1994, Biotechnology 12:899-903). Human antibodies can also be produced using transgenic mice that express human immunoglobulin genes. Monoclonal antibodies directed against the antigen can be obtained from the immunized, transgenic mice using hybridoma technology. For an overview of the technology for producing human antibodies, see Lonberg and Huszar, 1995, Int. Rev. Immunol. 13:65-93. For a detailed discussion of this technology for producing human antibodies and human monoclonal antibodies and protocols for producing such antibodies, see, e.g., Intl. Publ. Nos. WO 98/24893; WO 92/01047; WO 96/34096; WO 96/33735; European Patent No. 0598877; and U.S. Pat. Nos. 5,413,923; 5,625,126; 5,633,425; 5,569,825; 5,661,016; 5,545,806; 5,814,318; 5,885,793; 5,916,771; and 5,939,598.

Antibodies can be assayed for specific binding to folate receptor alpha by known methods, such as for example, competitive and non-competitive immunoassay systems using techniques such as Western blots, radioimmunoassays, ELISA (enzyme linked immunosorbent assay), "sandwich" immunoassays, immunoprecipitation assays, precipitation reactions, gel diffusion precipitation reactions, immunodiffusion assays, agglutination assays, complement-fixation assays, immunoradiometric assays, fluorescent immunoassays, protein A immunoassays. (See, e.g., Ausubel et al., eds., Short Protocols in Molecular Biology (John Wiley & Sons, Inc., New York, 4th ed. 1999); Harlow & Lane, Using Antibodies: A Laboratory Manual (Cold Spring Harbor Laboratory Press, Cold Spring Harbor, N.Y., 1999.)

Further, the binding affinity of an antibody to folate receptor alpha and the off-rate of an antibody-folate receptor alpha interaction can be determined by competitive binding assays. One example of a competitive binding assay is a radioimmunoassay comprising the incubation of labeled folate receptor alpha (e.g., $^3$H or $^{125}$I) with the antibody of interest in the presence of increasing amounts of unlabeled folate receptor alpha, and the detection of the antibody bound to the labeled folate receptor alpha. The affinity of the antibody for folate receptor alpha and the binding off-rates can then be determined from the data by Scatchard plot analysis. Competition with a second antibody can also be determined using radioimmunoassays. In this case, folate receptor alpha is incubated with the antibody of interest conjugated to a labeled compound (e.g., $^3$H or $^{125}$I) in the presence of increasing amounts of an unlabeled second antibody. Alternatively, the binding affinity of an antibody to folate receptor alpha and the on- and off-rates of an antibody-folate receptor alpha interaction can be determined by surface plasmon resonance.

Antibodies can be made from antigen-containing fragments of the folate receptor alpha protein by standard procedures according to the type of antibody (see, e.g., Kohler, et al., Nature, 256:495, (1975); Harlow & Lane, Antibodies, A Laboratory Manual (C.S.H.P., NY, 1988); Queen et al., Proc. Natl. Acad. Sci. USA 86:10029-10033

(1989) and WO 90/07861; Dower et al., WO 91/17271 and McCafferty et al., WO 92/01047 (each of which is incorporated by reference for all purposes). As an example, monoclonal antibodies can be prepared using a wide variety of techniques including, e.g., the use of hybridoma, recombinant, and phage display technologies, or a combination thereof. Hybridoma techniques are generally discussed in, e.g., Harlow et al., supra, and Hammerling, et al., In Monoclonal Antibodies and T-Cell Hybridomas, pp. 563-681 (Elsevier, N.Y., 1981). Examples of phage display methods that can be used to make the anti-folate receptor alpha antibodies include, e.g., those disclosed in Brinnan et al., 1995, J. Immunol. Methods 182:41-50; Ames et al., 1995, J. Immunol. Methods 184:177-186; Kettleborough et al., 1994, Eur. J. Immunol. 24:952-958; Persic et al., 1997, Gene 187:9-18; Burton et al., 1994, Advances in Immunology 57:191-280; PCT Application No. PCT/GB91/01 134; PCT Publications WO 90/02809; WO 91/10737; WO 92/01047; WO 92/18619; WO 93/11236; WO 95/15982; WO 95/20401; and U.S. Pat. Nos. 5,698,426; 5,223,409; 5,403,484; 5,580,717; 5,427,908; 5,750,753; 5,821,047; 5,571,698; 5,427,908; 5,516,637; 5,780,225; 5,658,727; 5,733,743 and 5,969,108 (the disclosures of which are incorporated by reference herein).

Techniques for generating antibody fragments that recognize specific epitopes are also generally known in the art. For example, Fab and F(ab')2 fragments can be produced by proteolytic cleavage of immunoglobulin molecules, using enzymes such as papain (to produce Fab fragments) or pepsin (to produce F(ab')2 fragments). F(ab')2 fragments contain the variable region, the light chain constant region and the CH1 domain of the heavy chain. Techniques to recombinantly produce Fab, Fab' and F(ab')2 fragments can also be employed using, e.g., methods disclosed in WO 92/22324; Mullinax et al., 1992, BioTechniques 12(6):864-869; and Sawai et al., 1995, AJRI 34:26-34; and Better et al., 1988, Science 240:1041-1043 (the disclosures of which are incorporated by reference herein).

Examples of techniques that can be used to produce single-chain Fvs and antibodies include those described in U.S. Pat. Nos. 4,946,778 and 5,258,498; Huston et al., 1991, Methods in Enzymology 203:46-88; Shu et al., 1993, Proc. Natl. Acad. Sci. USA 90:7995-7999; and Skerra et al., 1988, Science 240:1038-1040.

Anti-folate receptor alpha antibodies and derivatives thereof that are useful in the present methods can also be produced by recombinant expression techniques. Recombinant expression of an antibody or derivative thereof that binds to folate receptor alpha and/or depletes or inhibits the proliferation of folate receptor alpha-expressing cells requires construction of an expression vector containing a nucleic acid that encodes the antibody or derivative thereof. Once a nucleic acid encoding such a protein has been obtained, the vector for the production of the protein molecule may be produced by recombinant DNA technology using techniques well known in the art. Standard techniques such as those described in Sambrook and Russell, Molecular Cloning: A Laboratory Manual (Cold Spring Harbor Laboratory Press, Cold Spring Harbor, N.Y., 3rd ed., 2001); Sambrook et al., Molecular Cloning: A Laboratory Manual (Cold Spring Harbor Laboratory Press, Cold Spring Harbor, N.Y., 2nd ed., 1989); Ausubel et al., Short Protocols in Molecular Biology (John Wiley & Sons, New York, 4th ed., 1999); and Glick & Pasternak, Molecular Biotechnology: Principles and Applications of Recombinant DNA (ASM Press, Washington, D.C., 2nd ed., 1998) can be used for recombinant nucleic acid methods, nucleic acid synthesis, cell culture, transgene incorporation, and recombinant protein expression.

For example, for recombinant expression of an anti-folate receptor alpha antibody, an expression vector may encode a heavy and/or light chain thereof, or a heavy and/or light chain variable domain, operably linked to a promoter. An expression vector may include, e.g., the nucleotide sequence encoding the constant region of the antibody molecule (see, e.g., WO 86/05807; WO 89/01036; and U.S. Pat. No. 5,122,464), and the variable domain of the antibody may be cloned into such a vector for expression of the entire heavy or light chain. The expression vector is transferred to a host cell by known techniques, and the transfected cells are then cultured to produce the anti-folate receptor alpha antibody. Typically, for the expression of double-chained antibodies, vectors encoding both the heavy and light chains can be co-expressed in the host cell for expression of the entire immunoglobulin molecule.

A variety of prokaryotic and eukaryotic host-expression vector systems can be utilized to express an anti-folate receptor alpha antibody or derivative thereof. Typically eukaryotic cells, particularly for whole recombinant anti-folate receptor alpha antibody molecules, are used for the expression of the recombinant protein. For example, mammalian cells such as NS0 cells or Chinese hamster ovary cells (CHO) (e.g., DG44 or CHO-S) in conjunction with a promoter element such as the major intermediate early gene promoter element from human cytomegalovirus or the Chinese hamster ovary EF-1alpha promoter, is an effective expression system for the production of anti-folate receptor alpha antibodies and derivatives thereof (see, e.g., Foecking et al., 1986, Gene 45:101; Cockett et al., 1990, Bio/Technology 8:2; Allison, U.S. Pat. No. 5,888,809).

Other host-expression systems include, plasmid-based expression systems in bacterial cells (see, e.g., Ruther et al., 1983, EMBO 1, 2:1791; Inouye & Inouye, 1985, Nucleic Acids Res. 13:3101-3109; Van Heeke & Schuster, 1989, J. Biol. Chem. 24:5503-5509); insect systems such as the use of *Autographa californica* nuclear polyhedrosis virus (AcNPV) expression vector in *Spodoptera frugiperda* cells; and viral-based expression systems in mammalian cells, such as, adenoviral-based systems (see, e.g., Logan & Shenk, 1984, Proc. Natl. Acad. Sci. USA 81:355-359; Bittner et al., 1987, Methods in Enzymol. 153:51-544).

B. Antibodies for Detection of Folate Receptor Alpha-Expressing Gastric Cancer

A preferred antibody for detection of folate receptor alpha in gastric cancers is monoclonal antibody 26B3. Other preferred antibodies for detection of folate receptor alpha in gastric cancers compete with 26B3 for specific binding to folate receptor alpha. Other preferred antibodies for detection of folate receptor alpha in gastric cancers comprise a heavy chain comprising the three CDRs from the heavy chain of 26B3 and a light chain comprising the three CDRs from the light chain of 26B3 as shown in Table 1.

TABLE 1

Monoclonal antibody 26B3
(murine IgG1 constant region)

| Antibody segment | SEQ ID NO: | Amino acid sequence |
|---|---|---|
| CDRL1 | 9 | RTSENIFSYLA |
| CDRL2 | 10 | NAKTLAE |
| CDRL3 | 11 | QHHYAFPWT |
| LC variable domain segment | 12 | PASLSASVGETVTITCRTSENIFSYLAWYQQKQGISPQLLVYNAKTLAEGVPSRFSGSGSGTQFSLKINSLQPEDFGSYYCQHHYAFPWTFGGGSKLEIKRADAAP |
| CDRH1 | 13 | GYFMN |
| CDRH2 | 14 | RIFPYNGDTFYNQKFKG |
| CDRH3 | 15 | GTHYFDY |
| HC variable domain segment | 16 | GPELVKPGASVKISCKASDYSFTGYFMNWVMQSHGKSLEWIGRIFPYNGDTFYNQKFKGRATLTVDKSSSTAHMELRSLASEDSAVYFCARGTHYFDYWGQGTTLTVSSAKTTPPSVYPLAPGSAAQT |

Other preferred antibodies for detection of folate receptor alpha in gastric cancers comprise a mature heavy chain variable region having at least 90% sequence identity to the mature heavy chain variable region of 26B3 and a mature light chain variable region having at least 90% sequence identity to the mature light chain variable region of 26B3.

C. Antibodies to Folate Receptor Alpha for Therapeutic Applications

Antibodies used for therapeutic applications specifically bind to folate receptor alpha on gastric cancer cells. For example, the antibody is selected from the group consisting of:

(a) an antibody comprising SEQ ID NO:1 (GFTFSGYGLS) as CDRH1, SEQ ID NO:2 (MISSGGSYTYYADSVKG) as CDRH2, SEQ ID NO:3 (HGDDPAWFAY) as CDRH3, SEQ ID NO:4 (SVSSSISSNNLH) as CDRL1, SEQ ID NO:5 (GTSNLAS) as CDRL2 and SEQ ID NO:6 (QQWSSYPYMYT) as CDRL3; or (b) an antibody that binds the same epitope as the MORAb-003 antibody.

In some embodiments, the antibody comprises a mature light chain variable region comprising the amino acid sequence of SEQ ID NO:7:

```
  1  DIQLTQSPSS LSASVGDRVT ITCSVSSSIS SNNLHWYQQK PGKAPKPWIY

51  GTSNLASGVP SRFSGSGSGT DYTFTISSLQ PEDIATYYCQ QWSSYPYMYT

101  FGQGTKVEIK RTVAAPSVFI FPPSDEQLKS GTASVVCLLN NFYPREAKVQ

151  WKVDNALQSG NSQESVTEQD SKDSTYSLSS TLTLSKADYE KHKVYACEVT

201  HQGLSSPVTK SFNRGEC
(CDRs underlined).
```

In some embodiments, the antibody comprises a mature heavy chain variable region comprising the amino acid SEQ ID NO: 8:

```
  1  EVQLVESGGG VVQPGRSLRL SCSASGFTFS GYGLSWVRQA PGKGLEWVAM

51  ISSGGSYTYY ADSVKGRFAI SRDNAKNTLF LQMDSLRPED TGVYFCARHG

101  DDPAWFAYWG QGTPVTVSSA STKGPSVFPL APSSKSTSGG TAALGCLVKD

151  YFPEPVTVSW NSGALTSGVH TFPAVLQSSG LYSLSSVVTV PSSSLGTQTY

201  ICNVNHKPSN TKVDKKVEPK SCDKTHTCPP CPAPELLGGP SVFLFPPKPK

251  DTLMISRTPE VTCVVVDVSH EDPEVKFNWY VDGVEVHNAK TKPREEQYNS

301  TYRVVSVLTV LHQDWLNGKE YKCKVSNKAL RAPIEKTISK AKGQPREPQV

351  YTLPPSRDEL TKNQVSLTCL VKGFYPSDIA VEWESNGQPE NNYKTTPPVL

401  DSDGSFFLYS KLTVDKSRWQ QGNVFSCSVM HEALHNHYTQ KSLSLSPGK
(CDRs underlined).
```

In some embodiments, the antibody comprises a mature light chain variable region comprising the amino acid sequence of SEQ ID NO: 7 and a mature heavy chain variable region comprising the amino acid sequence of SEQ ID NO: 8. An example of such an antibody is MORAb-003. CHO cells producing MORAb-003 (USAN: farletuzumab) have been deposited with the ATCC University Boulevard, Manassas, Va. 20110) on Apr. 24, 2006 and assigned accession no. PTA-7552.

Other useful antibodies comprise mature light and heavy chain variable regions having at least 90% and preferably at least 95% or 99% sequence identity to SEQ ID NO: 7 and SEQ ID NO: 8, respectively. Other useful anti-folate receptor alpha antibodies or derivatives thereof can competitively inhibit binding of MORAb-003 to folate receptor alpha, as determined, for example, by immunoassay. Competitive inhibition means that an antibody when present in at least a two-fold and preferably five-fold excess inhibits binding of MORAb-003 to folate receptor alpha by at least 50%, more typically at least 60%, yet more typically at least 70%, and most typically at least 75%, at least 80%, at least 85%, at least 90%, or at least 95%.

A derivative of an anti-folate receptor alpha antibody can also be used in the practice of present methods. Typical modifications include, e.g., glycosylation, deglycosylation, acetylation, pegylation, phosphorylation, amidation, derivatization by known protecting/blocking groups, proteolytic cleavage, linkage to a cellular ligand or other protein, and the like. Additionally, the derivative may contain one or more non-classical amino acids.

The described anti-FRA antibodies and antigen-binding fragments may be detectably labeled. In some embodiments labeled antibodies and antigen-binding fragments may facilitate the detection FRA via the methods described herein. Many such labels are readily known to those skilled in the art. For example, suitable labels include, but should not be considered limited to, radiolabels, fluorescent labels (such as DyLight® 649), epitope tags, biotin, chromophore labels, ECL labels, or enzymes. More specifically, the described labels include ruthenium, $^{111}$In-DOTA, $^{111}$In-diethylenetriaminepentaacetic acid (DTPA), horseradish peroxidase, alkaline phosphatase and beta-galactosidase, polyhistidine (HIS tag), acridine dyes, cyanine dyes, fluorone dyes, oxazin dyes, phenanthridine dyes, rhodamine dyes, Alexafluor® dyes, and the like.

III. Detecting Folate Receptor Alpha

The samples to be assayed for diagnostic applications can be obtained by surgical procedures, e.g., biopsy. Folate receptor alpha is typically detected by an immunoassay in which a sample containing cells known or suspected to be from a cancer (e.g., gastric cancer) is contacted with an antibody or antigen-binding fragment. After contact, the presence or absence of a binding event of the antibody or antigen-binding fragment to the cells in the specimen is determined. The binding is related to the presence or absence of the antigen expressed on cancerous cells in this specimen. Generally, the sample is contacted with a labeled specific binding partner of the anti-folate receptor alpha antibody or antigen-binding fragment capable of producing a detectable signal. Alternatively, the anti-folate receptor alpha antibody or fragment itself can be labeled. Examples of types of labels include enzyme labels, radioisotopic labels, nonradioactive labels, fluorescent labels, toxin labels and chemoluminescent labels. Detection of a signal from the label indicates the presence of the antibody or fragment specifically bound to folate receptor alpha in the sample.

The described anti-FRA antibodies and antigen-binding fragments antibodies and antigen-binding fragments may be used in a variety of assays to detect FRA in a sample. Some suitable assays include, but should not be considered limited to, western blot analysis, radioimmunoassay, immunofluorimetry, immunoprecipitation, equilibrium dialysis, immunodiffusion, electrochemiluminescence (ECL) immunoassay, immunohistochemistry, fluorescence-activated cell sorting (FACS) or ELISA assay.

In some embodiments described herein detection of FRA-expressing gastric cancer cells in a subject may be used to determine that the subject may be treated with a therapeutic agent directed against FRA. In some embodiments the therapeutic agent directed against FRA may be an antibody, such as farletuzumab.

In some embodiments, detecting FRA in a sample, such as a histological sample, a fine needle aspirate sample, resected tumor tissue, circulating cells, circulating tumor cells, and the like, provides the ability to diagnose FRA-expressing gastric cancer in the subject from whom the sample was obtained. In some embodiments, it may already be known that the subject from whom the sample was obtained has cancer, but the type of cancer afflicting the subject may not yet have been diagnosed or a preliminary diagnosis may be unclear, thus detecting FRA in a sample obtained from the subject can allow for, or clarify, diagnosis of the cancer.

The sample on which the assay is performed can be fixed or frozen to permit histological sectioning. Preferably, the excised tissue samples are fixed in aldehyde fixatives such as formaldehyde, paraformaldehyde, glutaraldehyde; or heavy metal fixatives such as mercuric chloride. More preferably, the excised tissue samples are fixed in formalin and embedded in paraffin wax prior to incubation with the antibody. Optionally, FFPE specimens can be treated with citrate, EDTA, enzymatic digestion or heat to increase accessibility of epitopes.

Alternatively, a protein fraction can be isolated from cells from known or suspected gastric cancer and analyzed by ELISA, Western blotting, immunoprecipitation or the like. In another variation, cells can be analyzed for expression of folate receptor alpha by FACS analysis, preferably in combination with another gastric cancer cell marker.

In a further variation, mRNA can be extracted from cells from known or suspected gastric cancer. The mRNA or a nucleic acid derived therefrom, such as a cDNA can then be analyzed by hybridization to a nucleic probe binding to DNA encoding folate receptor alpha.

In another variation, a gastric cancer can be detected in vivo by administering a labeled anti-folate receptor alpha antibody or antigen-binding fragment thereof to a patient and detecting the antibody or fragment by in vivo imaging.

Detection of folate receptor alpha in tissue samples can be qualitative or quantitative or both. Qualitative detection means detecting the presence or absence of folate receptor alpha expression. Quantitative expression means determining a level of expression of folate receptor alpha. The presence and/or level of folate receptor alpha in a gastric tissue sample at issue can (but need not) be determined with respect to one or more standards. The standards can be historically or contemporaneously determined. The standard can be, for example, a gastric tissue sample known not to be cancerous from a different subject, a tissue from either the patient or other subject known not to express folate receptor alpha, or a gastric cell line. The standard can also be the patient sample under analysis contacted with an irrelevant antibody (e.g., an antibody raised to a bacterial antigen).

The presence of detectable signal from binding of an anti-folate receptor alpha antibody or fragment to folate receptor alpha relative to a standard (if used) indicates the presence of folate receptor alpha in the tissue sample, and the level of detectable binding provides an indication of the level of expression of folate receptor alpha. In assays performed on tissue sections, the level of expression can be expressed as a percentage of the surface area of the sample showing detectable expression of folate receptor alpha. Alternatively, or additionally, the level (intensity) of expression can be used as a measure of the total expression in the sample or of the cells expressing folate receptor alpha in the sample.

IV. Diagnosis, Prognosis, Designing and Monitoring Treatment

Detection of expression of folate receptor alpha in a sample of gastric tissue is an indication that the sample is cancerous. The indication of cancer provided by presence and/or level of folate receptor alpha can be combined with means of diagnosis, such as internal or external examination of a patient by a physician, stool test to check for blood in the stool, complete blood count to check for anemia, esophagogastroduodenoscopy with biopsy, X-ray, CT Scan (Computed Tomography), PET Scan (Positron Emission Tomography), PET/CT Scan, ultrasound, MRI (Magnetic Resonance Imaging), assays for beta-human chorionic gonadotropin, CA125, and/or carcinoembryonic antigen in the blood, endoscopy, laparoscopy, histological examination and tissue culturing in arriving at an overall diagnosis.

Perhaps of greatest relevance to the physician, the presence and level of folate receptor alpha provides useful information for designing a treatment protocol for the patient, and in particular administering an antibody against folate receptor alpha or an antigen-binding fragment thereof to a patient. The higher the level of folate receptor alpha expression and/or the higher percentage of a tumor expressing folate receptor alpha, the more effective treatment is likely to be. Continued analysis of folate receptor alpha after treatment provides a means of monitoring whether the treatment is effective, wherein stabilization or reduction in the level of folate receptor alpha-positive signal (i.e., as a proxy for the presence of folate receptor alpha-positive cancer cells) is indicative that the treatment is effective.

V. Patients Amenable to Treatment

Patients amenable to treatment by the methods usually have detectable levels of folate receptor alpha in their gastric tissue accompanied by other signs or symptoms of cancer as described above. A variety of subtypes and stages of gastric cancer exist as described in more detail below.

Sometimes, patients treated by the present methods have undergone other types of treatment previously (e.g., surgery, chemotherapy and/or radiation). In some cases, the prior treatment may not have induced remission or even slowed the growth of the cancer. In some such patients, the cancer is refractory to treatment by one of more such therapies.

Some patients at risk for gastric cancer can also be treated prophylactically before signs and symptoms of the disease appear. Such individuals include those having relatives who have experienced the disease, those whose risk is determined by analysis of genetic or biochemical markers, those having an *Helicobacter pylori* infection of the stomach, those who have had a polyp of the stomach larger than 2 centimeters, those who have had inflammation and swelling of the stomach for an extended time (chronic atrophic gastritis), those having habitual salt intake, those who use tobacco products, those who consume alcohol, and those identified as having pernicious anemia.

Individuals suffering from gastric cancer can be recognized according to the histology of the tumor, obtained in a pathology report. Histology dictates many aspects of clinical treatment, management, and prognosis. A majority of gastric tumors are adenocarcinomas (e.g., intestinal type; diffuse type; papillary; tubular; poorly differentiated; signet-ring cell; and mucinous adenocarcinoma). Other gastric tumors include soft tissue sarcomas (e.g., leiomyosarcomas and gastrointestinal stromal tumors), lymphomas (e.g., mucosa associated lymphoid tissue (MALT) lymphomas), carcinoid tumors, small cell neuroendocrine carcinoma.

Gastric cancer staging can be performed according to the TNM system. In stage 0 (carcinoma in situ), abnormal cells are found in the inside lining of the mucosa (innermost layer) of the stomach wall. These abnormal cells may become cancer and spread into nearby normal tissue. In stage I, cancer has formed in the inside lining of the mucosa (innermost layer) of the stomach wall. Stage I is divided into stage IA and stage IB, depending on where the cancer has spread. In stage IA, cancer may have spread into the submucosa (layer of tissue next to the mucosa) of the stomach wall, whereas in stage IB, cancer: may have spread into the submucosa of the stomach wall and is found in 1 or 2 lymph nodes near the tumor; or cancer has spread to the muscle layer of the stomach wall. Stage II gastric cancer is divided into stage IIA and stage IIB, depending on where the cancer has spread. In stage IIA, cancer has spread to the subserosa of the stomach wall; to the muscle layer of the stomach wall and is found in 1 or 2 lymph nodes near the tumor; or to the submucosa of the stomach wall and is found in 3 to 6 lymph nodes near the tumor. In stage IIB, cancer has spread to the serosa of the stomach wall; to the subserosa of the stomach wall and is found in 1 or 2 lymph nodes near the tumor; to the muscle layer of the stomach wall and is found in 3 to 6 lymph nodes near the tumor; or to the submucosa of the stomach wall and is found in 7 or more lymph nodes near the tumor. Stage III gastric cancer is divided into stage IIIA, stage IIIB, and stage IIIC, depending on where the cancer has spread. In Stage IIIA, cancer has spread to the serosa layer of the stomach wall and is found in 1 or 2 lymph nodes near the tumor; the subserosa of the stomach wall and is found in 3 to 6 lymph nodes near the tumor; or the muscle layer of the stomach wall and is found in 7 or more lymph nodes near the tumor. In stage IIIB, cancer has spread to nearby organs such as the spleen, transverse colon, liver, diaphragm, pancreas, kidney, adrenal gland, or small intestine, and may be found in 1 or 2 lymph nodes near the tumor; the serosa of the stomach wall and is found in 3 to 6 lymph nodes near the tumor; or the subserosa of the stomach wall and is found in 7 or more lymph nodes near the tumor. In stage IIIC, cancer has spread to nearby organs such as the spleen, transverse colon, liver, diaphragm, pancreas, kidney, adrenal gland, or small intestine, and may be found in 3 or more lymph nodes near the tumor; the serosa of the stomach wall and is found in 7 or more lymph nodes near the tumor. In stage IV, cancer has spread to distant parts of the body. An alternative to the TNM staging system is the three stage classification (potentially resectable, locally advanced and metastatic), which is based on radiological findings. Other prognosis factors are also considered. Gastric cancer grading also provides an indication of how abnormal the cells look under the microscope. The grade provides an indication of how quickly the cancer cells may develop, with grade 1 indicating slow growth (i.e., cells are well differentiated) and are less likely to spread than higher grades; grade 2 indicative of a more abnormal appearance and slightly faster growth; and grade 3, in which the cancer cells tend to grow more quickly, look very abnormal (are 'poorly differentiated') and are more likely to spread. For patients who have surgery (i.e., gastrectomy), the extent of the resection, i.e., whether or not all of the tumor is removed, is also important with regard to outlook. This is sometimes listed on a scale from RO to R2 with RO indicating that all of tumor that can be seen has been removed and R2 indicating that some tumor that can be seen cannot be removed.

Early gastric cancer symptoms are non-specific. Common symptoms include abdominal fullness or pain, which may occur after a small meal; dark stools; difficulty swallowing, which becomes worse over time; excessive belching; general decline in health; loss of appetite; nausea; vomiting, which may contain blood; weakness or fatigue; and/or weight loss.

VI. Methods of Treatment and Pharmaceutical Compositions

The present invention provides methods of treating or prophylaxis of gastric cancer by the antibodies and antigen-binding fragments (referred to collectively as the "agents" herein) disclosed herein, including but not limited to those described in Part II.C supra.

Various delivery systems can be used to administer the agents including intradermal, intramuscular, intraperitoneal, intravenous, subcutaneous, intranasal, epidural, and oral routes. The agents can be administered, for example by infusion or bolus injection, by absorption through epithelial or mucocutaneous linings (e.g., oral mucosa, rectal and intestinal mucosa, and the like). Administration can be systemic or local.

The agents can be administered by injection, by means of a catheter, by means of a suppository, or by means of an implant, the implant being of a porous, non-porous, or gelatinous material, including a membrane, such as a sialastic membrane, or a fiber.

Alternatively, the agents can be delivered in a controlled release system. For example, a pump can be used (see Langer, 1990, Science 249:1527-1533; Sefton, 1989, CRC Crit. Ref Biomed. Eng. 14:201; Buchwald et al., 1980, Surgery 88:507; Saudek et al., 1989, N. Engl. J. Med. 321:574). Alternatively, polymeric materials can be used (see Medical Applications of Controlled Release (Langer & Wise eds., CRC Press, Boca Raton, Fla., 1974); Controlled Drug Bioavailability, Drug Product Design and Performance (Smolen & Ball eds., Wiley, New York, 1984); Ranger & Peppas, 1983, Macromol. Sci. Rev. Macromol. Chem. 23:61. See also Levy et al., 1985, Science 228:190; During et al., 1989, Ann. Neurol. 25:351; Howard et al., 1989, J. Neurosurg. 71:105.) Other controlled release systems are discussed, for example, in Langer, supra.

The agents can be administered as pharmaceutical compositions comprising a therapeutically or prophylactically effective amount of the agent and one or more pharmaceutically compatible ingredients. For example, the pharmaceutical composition typically includes one or more pharmaceutical carriers (e.g., sterile liquids, such as water and oils, including those of petroleum, animal, vegetable or synthetic origin, such as peanut oil, soybean oil, mineral oil, sesame oil and the like). Water is a more typical carrier when the pharmaceutical composition is administered intravenously. Saline solutions (e.g., phosphate buffered saline) and aqueous dextrose and glycerol solutions can also be employed as liquid carriers, particularly for injectable solutions. Suitable pharmaceutical excipients include, for example, starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol, and the like. The composition, if desired, can also contain minor amounts of wetting or emulsifying agents, pH buffering agents (e.g., amino acids) and/or solubilizing or stabilizing agents (e.g., nonionic surfactants such as tween or sugars such as sucrose, trehalose or the like). These compositions can take the form of solutions, suspensions, emulsion, tablets, pills, capsules, powders, sustained-release formulations and the like. Also included are solid form preparations which are intended to be converted, shortly before use, to liquid preparations. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in "Remington's Pharmaceutical Sciences" by E. W. Martin. Such compositions will contain a therapeutically effective amount of the nucleic acid or protein, typically in purified form, together with a suitable amount of carrier so as to provide the form for proper administration to the patient. The formulations correspond to the mode of administration.

Typically, compositions for intravenous administration are solutions in sterile isotonic aqueous buffer. When necessary, the pharmaceutical can also include a solubilizing agent and a local anesthetic such as lignocaine to ease pain at the site of the injection. Generally, the ingredients are supplied either separately or mixed together in unit dosage form, for example, as a dry lyophilized powder or a concentrate in a hermetically sealed container such as an ampoule or sachette indicating the quantity of active agent. When the pharmaceutical composition is to be administered by infusion, it can be dispensed with an infusion bottle containing sterile pharmaceutical grade water or saline. When the pharmaceutical composition is administered by injection, an ampoule of sterile water for injection or saline can be provided so that the ingredients can be mixed prior to administration.

The antibodies and antigen-binding fragments and pharmaceutical compositions for use as described herein may be administered orally in any acceptable dosage form such as capsules, tablets, aqueous suspensions, solutions or the like. The antibodies and antigen-binding fragments and pharmaceutical compositions may also be administered parenterally including but not limited to: subcutaneous, intravenous, intramuscular, intra-articular, intra-synovial, intrasternal, intranasal, topically, intrathecal, intrahepatic, intralesional, and intracranial injection or infusion techniques. Generally the antibodies and antigen-binding fragments and pharmaceutical compositions will be administered intravenously or intraperitoneally, for example, by injection.

The amount of the agent that is effective in the treatment or prophylaxis of gastric cancer can be determined by standard clinical techniques. In addition, in vitro assays may optionally be employed to help identify optimal dosage ranges. The precise dose to be employed in the formulation also depends on the route of administration, and the stage of the cancer, and should be decided according to the judgment of the practitioner and each patient's circumstances. Effective doses may be extrapolated from dose-response curves derived from in vitro or animal model test systems. A dose can be formulated in animal models to achieve a circulating plasma concentration range that includes the $IC_{50}$ (i.e., the concentration of the test compound that achieves a half-maximal inhibition of symptoms) as determined in cell culture.

For example, toxicity and therapeutic efficacy of the agents can be determined in cell cultures or experimental animals by standard pharmaceutical procedures for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Agents that exhibit large therapeutic indices are preferred. When an agent exhibits toxic side effects, a delivery system that targets the agent to the site of affected tissue can be used to minimize potential damage to non-folate receptor alpha-expressing cells and, thereby, reduce side effects.

In some embodiments, the subject can be administered an antibody, antigen-binding fragment, or pharmaceutical composition described herein in a daily dose range of about 0.01 µg to about 500 mg per kg of the weight of the subject. Typically, the dosage of the agent administered to a patient with a folate receptor alpha-expressing gastric cancer is 0.1 mg/kg to 100 mg/kg of the subject's body weight. More typically, the dosage administered to a subject is 0.1 mg/kg to 10 mg/kg of the subject's body weight, even more typically 0.1 mg/kg to 5 mg/kg, or 0.1 mg/kg to 3 mg/kg of the subject's body weight. In some embodiments, the dosage of the agent (e.g., farletuzumab) administered to a subject having folate receptor alpha-expressing gastric cancer is about 2.5 mg/kg to about 10 mg/kg of the subject's body weight. Generally, human antibodies have a longer half-life within the human body than antibodies from other species due to the immune response to the foreign proteins. Thus, lower dosages of pharmaceutical composition comprising humanized, chimeric or human antibodies and less frequent administration is often possible.

The dose administered to the subject can also be measured in terms of total amount of the at least one antigen-binding protein administered per day. In some embodiments, a subject is administered about 5 to about 5000 milligrams of at least one antigen-binding protein per day. In some embodiments, a subject is administered up to about 10 milligrams of at least one antigen-binding protein per day. In some embodiments, a subject is administered up to about 100 milligrams of at least one antigen-binding protein per day. In some embodiments, a subject is administered up to about 250 milligrams of at least one antigen-binding protein per day. In some embodiments, a subject is administered up to about 500 milligrams of at least one antigen-binding protein per day. In some embodiments, a subject is administered up to about 750 milligrams of at least one antigen-binding protein per day. In some embodiments, a subject is administered up to about 1000 milligrams of at least one antigen-binding protein per day. In some embodiments, a subject is administered up to about 1500 milligrams of at least one antigen-binding protein per day. In some embodiments, a subject is administered up to about 2000 milligrams of at least one antigen-binding protein per day. In some embodiments, a subject is administered up to about 2500 milligrams of at least one antigen-binding protein per day. In some embodiments, a subject is administered up to about 3000 milligrams of at least one antigen-binding protein per day. In some embodiments, a subject is administered up to about 3500 milligrams of at least one antigen-binding protein per day. In some embodiments, a subject is administered up to about 4000 milligrams of at least one antigen-binding protein per day. In some embodiments, a subject is administered up to about 4500 milligrams of at least one antigen-binding protein per day. In some embodiments, a subject is administered up to about 5000 milligrams of at least one antigen-binding protein per day. In some embodiments, the antibody, antigen-binding fragment, or pharmaceutical composition is administered to a subject weekly or bi-weekly.

For effective treatment, one skilled in the art may recommend a dosage schedule and dosage amount adequate for the subject being treated. It may be preferred that dosing occur one to four or more times daily for as long as needed. The dosing may occur less frequently if the compositions are formulated in sustained delivery vehicles. The dosage schedule may also vary depending on the active drug concentration, which may depend on the needs of the subject.

The present methods can be combined with other means of treatment such as surgery, radiation, targeted therapy, chemotherapy, immunotherapy, use of growth factor inhibitors, or anti-angiogenesis factors. An anti-folate receptor alpha antibody or antigen-binding fragment thereof can be administered concurrently to a patient undergoing surgery, chemotherapy or radiation therapy treatments. Alternatively, a patient can undergo surgery, chemotherapy or radiation therapy prior or subsequent to administration of an anti-folate receptor alpha antibody or antigen-binding fragment thereof by at least an hour and up to several months, for example at least an hour, five hours, 12 hours, a day, a week, a month, or three months, prior or subsequent to administration of the antibody or antigen-binding fragment.

VII. Kits

The invention provides diagnostic kits for use with the above methods for detecting folate receptor-alpha-expressing gastric cancer. The kits typically contain an antibody or antigen-binding fragment thereof that specifically binds to folate receptor alpha (e.g., 26B3) useful for detection as described above. One or more additional containers may enclose elements, such as reagents or buffers, to be used in the assay. Such kits can also, or alternatively, contain a detection reagent that contains a reporter group suitable for direct or indirect detection of antibody binding.

The invention further provides pharmaceutical kits for treating folate receptor-alpha-expressing gastric cancer. Typically, such kits contain reagents (e.g., MORAb-003) formulated as a therapeutic composition as described herein, and can be in any of a variety of forms suitable for distribution in a kit. Such forms can include a liquid, powder, tablet, suspension and the like formulation for providing the anti-folate receptor alpha antibody or antigen-binding fragment. The kits can also include a pharmaceutically acceptable diluent (e.g., sterile water) for injection, reconstitution or dilution of the lyophilized antibody or fragment.

The invention further provides combined kits for diagnosis and therapy. Such kits typically include at least one antibody that binds to folate receptor alpha (e.g., 26B3) for use in detection in fixed tissue sections and a different antibody that binds to folate receptor alpha for use in treatment (e.g., MORAb-003).

Kits also typically contain a label or instructions for use in the methods of detection and/or treatment described herein. The label or instruction refers to any written or recorded material that is attached to, or otherwise accompanies a kit at any time during its manufacture, transport, sale or use. It can be a notice in the form prescribed by a governmental agency regulating the manufacture, use or sale of pharmaceuticals or biological products, which notice reflects approval by the agency of manufacture, use or sale for human administration. The label or instruction can also encompass advertising leaflets and brochures, packaging materials, instructions, audio or video cassettes, computer discs, as well as writing imprinted directly on the pharmaceutical kits.

The following examples are provided to further describe some of the embodiments disclosed herein. The examples are intended to illustrate, not to limit, the disclosed embodiments.

EXAMPLES

Example 1—Detection of FRA-Expressing Gastric Cancer Using Antibody 26B3

Immunohistochemistry (IHC) studies were conducted to determine binding to formalin fixed paraffin embedded (FFPE) tissue samples. Table 2 identifies the tissue samples included in the analysis. In particular, included are samples of gastric cancer metastasized ("gastric mets") to other specified tissues. For example, specimen #4 is a sample of gastric cancer metastasized to urinary bladder. FFPE serous ovarian carcinoma tissue was used as a positive control. Indirect IHC testing was performed for FRalpha using a MACH4™ Universal HRP-Polymer Detection Kit (Biocare Medical). Formalin-fixed paraffin-embedded specimens were sectioned at 5 microns on positively-charged glass slides and heated for approximately 60 minutes at 60° C. Slides were deparaffinized in 3 sequential baths of xylene for 3 minutes each, transferred to three sequential baths of 100% alcohol for 3 minutes each, followed by three sequential baths of 95% alcohol for 3 minutes each and then rinsed for 5 minutes in deionized (DI) water. Prepared samples were then pretreated with Diva heat-induced epitope retrieval solution (Biocare Medical) diluted to 1:10 in DI water and placed inside a pressurized decloaking chamber already filled with 500 ml of DI water. The samples were incubated for 15 minutes inside the decloaking chamber, where pressurized incubation reached a maximum of 125° C. at 16 PSI for 30 seconds and then was cooled for 15 minutes down to 95° C. Slides were then cooled at room temperature for 15 minutes. After cooling, slides were washed in 3 sequential baths of Tris Buffered Saline/0.1% Tween-20® wash buffer (TBST) for 3 minutes each. All subsequent buffer washes were also performed in this manner. Slides were then blocked in Peroxidase-1 (Biocare Medical) blocking solution for 5 minutes at room temperature, washed with TBST, and then Background Sniper (Biocare Medical) serum-free universal blocking reagent was applied for 10 minutes at room temperature. After the samples were blocked the slides were incubated with 2.5 µg/ml of 26B3 antibody diluted in Antibody Diluent (Dako) or Universal Negative Control—Mouse ready-to-use negative control antibody (Dako, for negative isotype tissue) for 60 minutes at room temperature. Slides were then washed with TBST and incubated with MACH4™ Mouse Probe Primary Antibody Enhancer (provided in the Biocare Medical MACH4™ kit) for 15 minutes at room temperature. Slides were then washed again with TBST and incubated with a Polymer-HRP reagent (provided in the Biocare Medical MACH4 kit) for 20 minutes at room temperature. Following incubation, slides were washed with TBST and incubated with a 3,3'-diaminobenzidine tetrahydrochloride (DAB) solution (Dako) for 5 minutes at room temperature. Then slides were thoroughly rinsed with DI water 3 times for 30-60 seconds each and counterstained with hematoxylin (Dako) for 2 minutes, washed with TBST, dehydrated in 3 sequential baths each of 95% and 100% alcohol for 30 seconds each, and cleared in 3 sequential baths of xylene for 30 seconds each. Finally, coverslips were applied to the slides prior to analysis. The expression of FRA was analyzed by a semi-quantitative scoring of immunohistochemical staining. Results are shown in Table 2.

As demonstrated by this example, antibody 26B3 can be used to detect FRA-expressing gastric cancer.

Example 2—Treatment of Gastric Cancer Using MORAb-003

Farletuzumab is a humanized monoclonal antibody directed against folate receptor α (FRA). It has been shown to mediate tumor cytotoxicity via antibody dependent cell cytotoxicity (ADCC) and complement dependent cytotoxicity (CDC) of a FRA-expressing human ovarian cancer cell line in vitro and to reduce tumor growth in FRA-expressing human ovarian cancer cells in vivo in a xenograft model (Ebel et al. (2007) Cancer Immun 7: 6). Expression of FRA is reported to be 40% in gastric cancer.

A phase I, open label, dose-escalation study of treatment of FRA-expressing solid tumor was conducted after obtaining written informed consent at the Saitama Medical University International Medical Center and National Cancer Center Hospital in Japan to monitor dose-limiting toxicity (DLT) and estimate maximum tolerated dose (MTD) as the primary objectives. The main inclusion criteria for the study included age 20≤ to <80 years; patients with solid tumor who are not responsive or are resistant to standard therapy and have no other appropriate treatment; FRA-positive tumor confirmed by IHC; patients with normal major organ function; no carry-over effect of prior treatment(s) and adverse drug reaction; Performance Status (PS) of 0 to 1 by Eastern Cooperative Oncology Group (ECOG). The main exclusion criteria for the study included: brain metastasis presenting clinical symptoms or requiring medical treatment; HIV, HCV antibody or HBs antigen positive; serious infection requiring medical treatment; history of hypersensitivity to monoclonal antibody or protein formulation; synchronous other active malignancy; or pleural effusion or ascites requiring drainage.

Two gastric cancer patients with FRA-expressing solid tumor who are resistant to standard treatments participated in the study. After a single farletuzumab administration for pharmacokinetic evaluation, farletuzumab was administered by intravenous injection repeating every week until disease progression. Specifically, farletuzumab was administered by intravenous drip infusion at a dose of 400 mg/m$^2$ in Cycle 0 (a single dose) and was administered from Cycle 1 (repeated-dose) once a week for 4 weeks (on days 1, 8, 15, and 22) as one cycle. Farletuzumab administration continued until subjects met the discontinuation criteria, including evidence of disease progression or appearance of new lesion(s). Serum farletuzumab concentrations were determined by enzyme-linked immunosorbent assay (ELISA).

Pharmacokinetic parameters were analyzed using WinNonlin™ (Version 6.2.1). Serum human anti-human antibody (HAHA) levels were assayed by ELISA. FRA expression was assessed by IHC. Immunoreactive intensity was classified as no reaction (−), weak (+: light brown with thin rim along the cell membrane), moderate (++: deep-brown with thin rim along the cell membrane), or strong (+++: deep-brown or higher intensity with thick rim along the cell membrane).

Results: Two gastric cancer patients (patient #10: male, age 71, FRA Staining intensity, +; patient #16: male, age 63, FRA staining intensity, +) received farletuzumab infusion. The FRA-expressing solid tumor of patient #16 was resistant to standard treatments including first-line therapy S-1 (Taiho Pharmaceutical Co Ltd., Japan) and second-line therapy docetaxel. Long-term disease stabilization for 20 months was observed in one patient (patient #16) with gastric cancer. No cumulative toxicity was observed in this patient. FIG. 1 shows the change in the sum of the longest diameter of tumor and level of tumor marker CEA in gastric cancer patient #16.

CONCLUSION

Although tumor shrinkage was not observed, significant tumor stabilization was identified in one FRA-expressing gastric cancer patient. Long-term disease stabilization was observed in a subpopulation of gastric cancer.

TABLE 2

| | | GENERAL SPECIMEN INFORMATION | | | | TEST ARTICLE-MEMBRANE STAINING OF NEO-PLASTIC CELLS % cells staining at each intensity | | | | TEST ARTICLE-OTHER SUB-CELLULAR STAINING OF NEO-PLASTIC CELLS % cells staining at each intensity | | | | TEST ARTICLE STAINING OF OTHER CELL TYPES & TUMOR INFORMATION | | | | | |
|---|---|---|---|---|---|---|---|---|---|---|---|---|---|---|---|---|---|---|---|
| Specimen ID # | Tissue | Histologic Review | Negative Isotype Control | Reject | Repeat | 3+ | 2+ | 1+ | 0 | 3+ | 2+ | 1+ | 0 | Normal | Endothelium | Stroma | Smooth Muscle | Inflam Cells | Nerve |
| 1 | Ovary CA | Serous CA | 0 | | | 90 | 10 | 0 | 0 | 50 | 40 | 10 | 0 | 0 | 0 | 0 | 0 | 0 | NS |
| 2 | Sacral Region, gastric mets | Solid CA | NA | | | 0 | 0 | 0 | 100 | 0 | 0 | 0 | 100 | 0 | NS | NS | NS | 0 | NS |
| 3 | Left supraclavicular node, gastric mets | Solid CA | NA | | | 20 | 20 | 10 | 50 | 20 | 40 | 20 | 20 | NS | 0 | 0 | 0 | 0 | NS |
| 4 | Urinary bladder, gastric mets | Signet ring CA | NA | | | 0 | 0 | 0 | 100 | 0 | 0 | 0 | 100 | 1+ | 0 | 0 | 0 | 0 | NS |
| 5 | Ascites, gastric mets | Adeno CA | NA | | | 10 | 10 | 10 | 70 | 0 | 0 | 10 | 90 | NS | NS | NS | NS | 0 | NS |
| 6 | Peritoneum, gastric mets | Signet ring CA | NA | | | 0 | 0 | 0 | 100 | 0 | 0 | 0 | 100 | 0 | NS | NS | NS | 0 | NS |
| 7 | Ascitic Fluid, gastric mets | Adeno CA | NA | | | 0 | 0 | 0 | 100 | 0 | 0 | 0 | 100 | 0 | NS | NS | NS | 0 | NS |
| 8 | Liver, gastric mets | Adeno CA | NA | | | 0 | 0 | 0 | 100 | 0 | 0 | 0 | 100 | 0 | 0 | 0 | 0 | 0 | NS |
| 9 | Peritoneal fluid, gastric mets | Adeno CA | NA | | | 0 | 0 | 0 | 100 | 0 | 0 | 0 | 100 | NS | NS | NS | NS | 0 | NS |
| 10 | Left neck, gastric mets | Solid Adeno CA | NA | | | 10 | 10 | 10 | 70 | 0 | 10 | 30 | 60 | NS | 0 | 0 | 0 | 0 | NS |
| 11 | Stomach, gastric mets | Adeno CA | NA | | | 0 | 0 | 0 | 100 | 0 | 0 | 0 | 100 | 1+ | 0 | 0 | NS | 0 | NS |
| 12 | Cerebellum, gastric mets | Adeno CA | NA | | | 0 | 0 | 0 | 100 | 0 | 0 | 0 | 100 | NS | 0 | 0 | NS | 0 | NS |
| 13 | Omentum, gastric mets | Signet ring CA | NA | | | 0 | 0 | 0 | 100 | 0 | 0 | 0 | 100 | NS | 0 | 0 | 0 | 0 | NS |

TABLE 2-continued

| | | | | | TEST ARTICLE-MEMBRANE STAINING OF NEOPLASTIC CELLS % cells | | | | TEST ARTICLE-OTHER SUBCELLULAR STAINING OF NEOPLASTIC CELLS % cells | | | | TEST ARTICLE STAINING OF OTHER CELL TYPES & TUMOR INFORMATION | | | | | |
|---|---|---|---|---|---|---|---|---|---|---|---|---|---|---|---|---|---|---|
| GENERAL SPECIMEN INFORMATION | | | | | | | | | | | | | | | | | | |
| Specimen ID # | Tissue | Histologic Review | Negative Isotype Control | Reject | Repeat | staining at each intensity | | | | staining at each intensity | | | | Normal | Endothelium | Stroma | Smooth Muscle | Inflam Cells | Nerve |
| | | | | | | 3+ | 2+ | 1+ | 0 | 3+ | 2+ | 1+ | 0 | | | | | | |
| 14 | Liver, gastric mets | Adeno CA | NA | | | 0 | 0 | 0 | 100 | 0 | 0 | 2 | 98 | NS | 0 | 0 | NS | NS | NS |
| 15 | Right ovary and omentum, gastric mets | Signet ring CA | NA | | | 0 | 0 | 0 | 100 | 0 | 5 | 5 | 90 | 2+ | 0 | 0 | 0 | NS | NS |
| 16 | Gastrointestinal tract, gastric mets | Adeno CA | NA | | | 60 | 10 | 10 | 20 | 40 | 30 | 30 | 0 | NS | 0 | 0 | 0 | 0 | NS |
| 17 | Liver, gastric mets | Adeno CA | NA | | | 0 | 10 | 10 | 80 | 0 | 10 | 20 | 70 | NS | NS | NS | NS | 0 | NS |
| 18 | Mesenteric lymph node, gastric mets | Signet ring CA | NA | | | 10 | 10 | 10 | 70 | 10 | 20 | 20 | 50 | NS | 0 | 0 | 0 | 0 | NS |
| 19 | Right upper lobe of lung, gastric mets | Adeno CA | NA | | | 0 | 0 | 0 | 100 | 0 | 0 | 0 | 100 | 3+ | 0 | 0 | 0 | 0 | NS |
| 20 | Peritoneum, gastric mets | Ascites | NA | X | | No malignant cells present | | | | | | | | | | | | | |
| 21 | Peritoneum, gastric mets | Signet ring CA | NA | | | 0 | 0 | 0 | 100 | 0 | 0 | 0 | 100 | NS | 0 | 0 | 0 | 0 | NS |
| 22 | Ascitic fluid, gastric mets | Adeno CA | NA | | | 0 | 0 | 0 | 100 | 0 | 0 | 0 | 100 | NS | NS | NS | NS | 0 | NS |
| 23 | Right upper lobe of lung, gastric mets | Adeno CA | NA | | | 0 | 0 | 0 | 100 | 0 | 0 | 0 | 100 | 2+ | 0 | 0 | 0 | 0 | NS |
| 24 | Bone, gastric mets | Adeno CA | NA | | | 0 | 0 | 0 | 100 | 0 | 0 | 0 | 100 | NS | 0 | 0 | NS | 0 | NS |
| 25 | Cervical lymph node, gastric mets | Adeno CA | NA | | | 0 | 0 | 0 | 100 | 0 | 0 | 0 | 100 | NS | 0 | 0 | 0 | 0 | NS |
| 26 | Left Pleura, gastric mets | Signet ring CA | NA | | | 0 | 0 | 0 | 100 | 0 | 0 | 0 | 100 | NS | 0 | 0 | 0 | 0 | NS |

TABLE 2-continued

| Specimen ID # | Tissue | Histologic Review | Negative Isotype Control | Reject | Repeat | TEST ARTICLE-MEMBRANE STAINING OF NEOPLASTIC CELLS % cells staining at each intensity | | | | TEST ARTICLE-OTHER SUBCELLULAR STAINING OF NEOPLASTIC CELLS % cells staining at each intensity | | | | TEST ARTICLE STAINING OF OTHER CELL TYPES & TUMOR INFORMATION | | | | | |
|---|---|---|---|---|---|---|---|---|---|---|---|---|---|---|---|---|---|---|---|
| | | | | | | 3+ | 2+ | 1+ | 0 | 3+ | 2+ | 1+ | 0 | Normal | Endothelium | Stroma | Smooth Muscle | Inflam Cells | Nerve |
| 27 | Ascites, gastric mets | Adeno CA | NA | | | 0 | 0 | 0 | 100 | 0 | 0 | 0 | 100 | NS | NS | NS | NS | 3+ | NS |
| 28 | Omentum, gastric mets | Signet ring CA | NA | | | 0 | 0 | 0 | 100 | 5 | 5 | 0 | 90 | NS | 0 | 0 | 0 | 3+ | NS |
| 29 | Right iliac bone, gastric mets | Necrotic Bone | NA | X | | No tumor cells present | | | | | | | | | | | | | |
| 30 | Left lung, gastric mets | Blood Clot | NA | X | | No tumor cells present | | | | | | | | | | | | | |
| 31 | Retroperitoneum, gastric mets | Solid CA | NA | | | 0 | 0 | 0 | 100 | 0 | 0 | 0 | 100 | NS | 0 | 0 | 0 | 0 | NS |

± = Equivocal Results
NA = Not Applicable
NS = Not Seen
Ap = Apical Staining
B = Basal Layer Staining
C = Cytoplasmic Staining
F = Focally Positive
La = Luminal Accentuation
H = Heterogeneous Staining
I = Inflammatory Cells
M = Membrane Staining
N = Nuclear Staining
P = Perineural Staining
S = Stroma
Sc = Scattered
c/w = Consistent With

What is claimed:

1. A method of detecting and treating folate receptor-alpha-expressing gastric cancer in a subject in need thereof comprising:
   detecting folate receptor alpha-expressing gastric cancer in a biological sample of the subject wherein the detecting comprises exposing the biological sample to a first antibody that specifically binds folate receptor alpha, wherein the first antibody comprises a heavy chain CDR1 (CDRH1) comprising the amino acid sequence of SEQ ID NO: 13, heavy chain CDR2 (CDRH2) comprising the amino acid sequence of SEQ ID NO: 14, heavy chain CDR3 (CDRH3) comprising the amino acid sequence of SEQ ID NO: 15, light chain CDR1 (CDRL1) comprising the amino acid sequence of SEQ ID NO: 9, light chain CDR2 (CDRL2) comprising the amino acid sequence of SEQ ID NO: 10, and light chain CDR3 (CDRL3) comprising the amino acid sequence of SEQ ID NO: 11, or an antigen-binding fragment thereof, and administering to the subject a therapeutically effective amount of a second antibody that specifically binds folate receptor alpha, wherein the second antibody comprises a CDRH1 comprising the amino acid sequence of SEQ ID NO: 1; CDRH2 comprising the amino acid sequence of SEQ ID NO: 2; CDRH3 comprising the amino acid sequence of SEQ ID NO: 3; CDRL1 comprising the amino acid sequence of SEQ ID NO: 4; CDRL2 comprising the amino acid sequence of SEQ ID NO: 5; and CDRL3 comprising the amino acid sequence of SEQ ID NO:6, or an antigen-binding fragment thereof.

2. The method of claim 1 wherein the first antibody or antigen-binding fragment is affixed to a solid support.

3. The method of claim 1 wherein the first antibody or antigen-binding fragment comprises a detectable label.

4. The method of claim 1 wherein the detecting comprises western blot analysis, radioimmunoassay, immunofluorimetry, immunoprecipitation, equilibrium dialysis, immunodiffusion, electrochemiluminescence (ECL) immunoassay, immunohistochemistry, fluorescence-activated cell sorting (FACS), or enzyme-linked immunosorbent assay (ELISA).

5. The method of claim 1 wherein the biological sample comprises a histological sample, a fine needle aspirate sample, resected tumor tissue, circulating cells, or circulating tumor cells.

6. The method of claim 1 wherein the step of administering comprises intravenous injection.

7. The method of claim 1 wherein the step of administering comprises weekly administration to the subject.

8. The method of claim 1 wherein the second antibody or antigen-binding fragment is administered at a dosage of about 50 mg/m$^2$ to about 400 mg/m$^2$.

9. The method of claim 1 wherein the second antibody or antigen-binding fragment is administered at a dosage of about 400 mg/m$^2$.

10. The method of claim 1 wherein the second antibody is farletuzumab.

* * * * *

SEQUENCE LISTING

<160> NUMBER OF SEQ ID NOS: 16

<210> SEQ ID NO 1
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 1

Gly Phe Thr Phe Ser Gly Tyr Gly Leu Ser
1               5                   10

<210> SEQ ID NO 2

```
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 2

Met Ile Ser Ser Gly Gly Ser Tyr Thr Tyr Tyr Ala Asp Ser Val Lys
1               5                   10                  15

Gly

<210> SEQ ID NO 3
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 3

His Gly Asp Asp Pro Ala Trp Phe Ala Tyr
1               5                   10

<210> SEQ ID NO 4
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 4

Ser Val Ser Ser Ser Ile Ser Ser Asn Asn Leu His
1               5                   10

<210> SEQ ID NO 5
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 5

Gly Thr Ser Asn Leu Ala Ser
1               5

<210> SEQ ID NO 6
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 6

Gln Gln Trp Ser Ser Tyr Pro Tyr Met Tyr Thr
1               5                   10

<210> SEQ ID NO 7
<211> LENGTH: 217
<212> TYPE: PRT
```

<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 7

```
Asp Ile Gln Leu Thr Gln Ser Pro Ser Ser Leu Ser Ala Ser Val Gly
1               5                   10                  15

Asp Arg Val Thr Ile Thr Cys Ser Val Ser Ser Ser Ile Ser Ser Asn
            20                  25                  30

Asn Leu His Trp Tyr Gln Gln Lys Pro Gly Lys Ala Pro Lys Pro Trp
        35                  40                  45

Ile Tyr Gly Thr Ser Asn Leu Ala Ser Gly Val Pro Ser Arg Phe Ser
50                  55                  60

Gly Ser Gly Ser Gly Thr Asp Tyr Thr Phe Thr Ile Ser Ser Leu Gln
65                  70                  75                  80

Pro Glu Asp Ile Ala Thr Tyr Tyr Cys Gln Gln Trp Ser Ser Tyr Pro
                85                  90                  95

Tyr Met Tyr Thr Phe Gly Gln Gly Thr Lys Val Glu Ile Lys Arg Thr
            100                 105                 110

Val Ala Ala Pro Ser Val Phe Ile Phe Pro Pro Ser Asp Glu Gln Leu
        115                 120                 125

Lys Ser Gly Thr Ala Ser Val Val Cys Leu Leu Asn Asn Phe Tyr Pro
130                 135                 140

Arg Glu Ala Lys Val Gln Trp Lys Val Asp Asn Ala Leu Gln Ser Gly
145                 150                 155                 160

Asn Ser Gln Glu Ser Val Thr Glu Gln Asp Ser Lys Asp Ser Thr Tyr
                165                 170                 175

Ser Leu Ser Ser Thr Leu Thr Leu Ser Lys Ala Asp Tyr Glu Lys His
            180                 185                 190

Lys Val Tyr Ala Cys Glu Val Thr His Gln Gly Leu Ser Ser Pro Val
        195                 200                 205

Thr Lys Ser Phe Asn Arg Gly Glu Cys
    210                 215
```

<210> SEQ ID NO 8
<211> LENGTH: 449
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 8

```
Glu Val Gln Leu Val Glu Ser Gly Gly Gly Val Val Gln Pro Gly Arg
1               5                   10                  15

Ser Leu Arg Leu Ser Cys Ser Ala Ser Gly Phe Thr Phe Ser Gly Tyr
            20                  25                  30

Gly Leu Ser Trp Val Arg Gln Ala Pro Gly Lys Gly Leu Glu Trp Val
        35                  40                  45

Ala Met Ile Ser Ser Gly Gly Ser Tyr Thr Tyr Tyr Ala Asp Ser Val
50                  55                  60

Lys Gly Arg Phe Ala Ile Ser Arg Asp Asn Ala Lys Asn Thr Leu Phe
65                  70                  75                  80

Leu Gln Met Asp Ser Leu Arg Pro Glu Asp Thr Gly Val Tyr Phe Cys
                85                  90                  95
```

Ala Arg His Gly Asp Asp Pro Ala Trp Phe Ala Tyr Trp Gly Gln Gly
            100                 105                 110

Thr Pro Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys

<210> SEQ ID NO 9
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

```
<400> SEQUENCE: 9

Arg Thr Ser Glu Asn Ile Phe Ser Tyr Leu Ala
1               5                   10

<210> SEQ ID NO 10
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 10

Asn Ala Lys Thr Leu Ala Glu
1               5

<210> SEQ ID NO 11
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 11

Gln His His Tyr Ala Phe Pro Trp Thr
1               5

<210> SEQ ID NO 12
<211> LENGTH: 106
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 12

Pro Ala Ser Leu Ser Ala Ser Val Gly Glu Thr Val Thr Ile Thr Cys
1               5                   10                  15

Arg Thr Ser Glu Asn Ile Phe Ser Tyr Leu Ala Trp Tyr Gln Gln Lys
            20                  25                  30

Gln Gly Ile Ser Pro Gln Leu Leu Val Tyr Asn Ala Lys Thr Leu Ala
        35                  40                  45

Glu Gly Val Pro Ser Arg Phe Ser Gly Ser Gly Ser Gly Thr Gln Phe
    50                  55                  60

Ser Leu Lys Ile Asn Ser Leu Gln Pro Glu Asp Phe Gly Ser Tyr Tyr
65                  70                  75                  80

Cys Gln His His Tyr Ala Phe Pro Trp Thr Phe Gly Gly Gly Ser Lys
                85                  90                  95

Leu Glu Ile Lys Arg Ala Asp Ala Ala Pro
            100                 105

<210> SEQ ID NO 13
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 13
```

```
Gly Tyr Phe Met Asn
1               5

<210> SEQ ID NO 14
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 14

Arg Ile Phe Pro Tyr Asn Gly Asp Thr Phe Tyr Asn Gln Lys Phe Lys
1               5                   10                  15

Gly

<210> SEQ ID NO 15
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 15

Gly Thr His Tyr Phe Asp Tyr
1               5

<210> SEQ ID NO 16
<211> LENGTH: 128
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 16

Gly Pro Glu Leu Val Lys Pro Gly Ala Ser Val Lys Ile Ser Cys Lys
1               5                   10                  15

Ala Ser Asp Tyr Ser Phe Thr Gly Tyr Phe Met Asn Trp Val Met Gln
                20                  25                  30

Ser His Gly Lys Ser Leu Glu Trp Ile Gly Arg Ile Phe Pro Tyr Asn
            35                  40                  45

Gly Asp Thr Phe Tyr Asn Gln Lys Phe Lys Gly Arg Ala Thr Leu Thr
        50                  55                  60

Val Asp Lys Ser Ser Ser Thr Ala His Met Glu Leu Arg Ser Leu Ala
65                  70                  75                  80

Ser Glu Asp Ser Ala Val Tyr Phe Cys Ala Arg Gly Thr His Tyr Phe
                85                  90                  95

Asp Tyr Trp Gly Gln Gly Thr Thr Leu Thr Val Ser Ser Ala Lys Thr
            100                 105                 110

Thr Pro Pro Ser Val Tyr Pro Leu Ala Pro Gly Ser Ala Ala Gln Thr
        115                 120                 125
```